United States Patent
Ulmer

(10) Patent No.: US 6,197,908 B1
(45) Date of Patent: Mar. 6, 2001

(54) HIGH MOLECULAR WEIGHT, HOMOGENEOUS, BRANCHED COPOLYMERS OF MALEIC ANHYDRIDE AND ALKYL VINYL ETHER MONOMERS

(75) Inventor: Herbert W. Ulmer, Hoboken, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/263,450

(22) Filed: Mar. 5, 1999

(51) Int. Cl.⁷ .................................................. C08F 116/12
(52) U.S. Cl. .......................... 526/332; 526/314; 526/266; 526/270; 526/271
(58) Field of Search ................................. 526/314, 332, 526/266, 270, 271

(56) References Cited

U.S. PATENT DOCUMENTS

| | | | |
|---|---|---|---|
| 4,521,551 | * | 6/1985 | Chang et al. .......................... 523/120 |
| 5,093,387 | * | 3/1992 | Schobel et al. ....................... 523/120 |
| 5,561,177 | * | 10/1996 | Khaledi et al. ........................ 524/35 |

* cited by examiner

*Primary Examiner*—Helen L. Pezzuto
(74) *Attorney, Agent, or Firm*—Walter Katz; William J. Davis; Marilyn J. Maue

(57) ABSTRACT

What is described is a high molecular weight homogeneous, branched copolymer of maleic anhydride and a $C_1$–$C_5$ alkyl vinyl ether monomer, in which a branching agent is present in an amount of less than 0.5 wt. % of the polymer. A solution process of making such polymer also is described.

10 Claims, No Drawings

HIGH MOLECULAR WEIGHT, HOMOGENEOUS, BRANCHED COPOLYMERS OF MALEIC ANHYDRIDE AND ALKYL VINYL ETHER MONOMERS

BACKGROUND OF THE INVENTION

1. Field of the Invention

This invention relates to copolymers of maleic anhydride and alkyl vinyl ethers, and more particularly, to high molecular weight, homogeneous, branched copolymers of such monomers, and to a solution process of making these polymers, and then use in denture adhesive compositions and personal care formulations.

2. Description of the Prior Art

Copolymers of maleic anhydride and alkyl vinyl ethers are well known in the art. Often, such polymers are prepared by precipitation polymerization in a solvent having a low chain transfer constant, such as benzene or cyclohexane. For example, high molecular weight, linear copolymers of methyl vinyl ether and maleic anhydride can be prepared by precipitation polymerization in benzene, and drying. Usually such precipitation process can be conducted at only a low solids levels, e.g. 20% solids or less.

Accordingly, it is an object of this invention to provide high molecular weight, homogeneous, branched copolymers of maleic anhydride and alkyl vinyl ethers.

Another object of this invention is to provide a solution polymerization process to prepare such high molecular weight, homogeneous, branched copolymers of maleic anhydride and alkyl vinyl ether monomers, in solvents other than benzene, and at a high solids levels, i.e. greater than 30%.

These and other objects and features of the invention will be made apparent from the following description of the invention.

SUMMARY OF THE INVENTION

What is described herein is a high molecular weight, homogeneous, branched copolymer of maleic anhydride and a $C_1$–$C_5$ alkyl vinyl ether monomer, in which the polymer chains are branched with a branching agent present in an amount of less than 0.5 wt. % of the polymer. Suitable polymers herein include those in which the maleic anhydride component is present in the form of its half-ester or diacid derivatives, having a molecular weight of greater than 100,000, preferably greater than 500,000. These polymers are made as a solution of the polymer at a concentration greater than 30% solids, in a non-benzene solvent such as acetone.

The copolymers of the invention are particularly useful in personal care and oral care compositions, for example, in denture adhesive compositions which include about 30–40% by wt. of the polymer.

DETAILED DESCRIPTION OF THE INVENTION

In accordance with the present invention, there is provided a high molecular weight homogeneous, branched polymer of maleic anhydride and a $C_1$–$C_5$ alkyl vinyl ether monomer, in which the polymer chains are branched with a branching agent present in an amount of less than 0.5 wt. % of the polymer.

As a feature of the invention, there is provided herein a solution polymerization process of making such copolymers. The process includes polymerizing maleic anhydride and an excess of an alkyl vinyl ether over 1:1 stoichiometry of the monomers, in a non-benzene solvent, in the presence of a branching agent present in an amount of less than 0.5 wt. % of the resultant polymer. A preferred non-benzene solvent is acetone, although other solvents in which the reaction product is soluble are also suitable, such as tetrahydrofuran, N-methyl pyrrolidone and the like.

As another feature of the invention, the process can be carried out at a >30% solids level.

Following polymerization, the resultant polymer can be converted to the half-ester or diacid derivative, if desired.

Suitable branching agents are those having a reactivity about the same as maleic anhydride so that all the branching agent and maleic anhydride are consumed in the presence of excess alkyl vinyl ether.

Suitable branching agents include phenylene and/or alkyl dimaleimides, dimaleic anhydrides and alkyl divinyl ethers.

The molecular weight of the copolymer product of the invention is greater than 100,000, preferably greater than 500,000 and, most preferably, greater than 1,000,000.

A preferred alkyl vinyl ether is methyl vinyl ether.

After completion of polymerization, the excess alkyl vinyl ether can be removed to provide the desired polymer in solution.

The copolymers of the invention are used in personal care and oral care compositions, for example, in denture adhesives which include about 30–40% by wt. of the polymer.

The invention will now be described with particular reference to the following examples, in which:

EXAMPLE 1

Copolymer of Maleic Anhydride-Methyl Vinyl Ether +N,N'-1,3-Phenylenedimaleimide (mole ratio 49.975:50.025:0.025)

A 2-liter stainless steel high pressure reactor was charged with 513.88 g of acetone and 0.201 g of N,N'-1,3-phenylenedimaleimide. The reactor was sealed and purged three times with nitrogen gas ending with a head pressure of 25 psi $N_2$. Then the temperature was raised to 70° C. during a 40 min period. When the temperature reached 60° C., 111.88 ml of molten maleic anhydride was introduced. At 80° C, separate feeds of 175.35 ml of methyl vinyl ether and 1.17 g of decanoyl peroxide in 33 g of acetone were introduced into the reactor over a period of 3 hours, with the methyl vinyl ether feed begun 10 min. before the decanoyl peroxide-acetone solution. After the feed was completed, the reactor was maintained at 80° C. for an additional half-hour. The reactor was then cooled to provide a thick, viscous light amber colored solution of the desired copolymer product in acetone.

EXAMPLE 2

The process of Example 1 was carried out at a polymerization temperature of 70° C. After polymerization was complete, the maleic anhydride polymer product was hydrolyzed with excess water to provide the maleic anhydride diacid derivative of the copolymer. Then the diacid was neutralized using 70 mol % $CaCO_3$ and 10 mol % $Na_2CO_3$ as follows: To 580.61 of the copolymer solution containing 19.281% solids of the diacid polymer in water a slurry of 44.988 g $CaCO_3$ and 6.812 g $Na_2CO_3$ in 300 g water was added under high agitation during 2 days. The product was the salt form of the diacid polymer which was oven-dried to provide the polymer in solid form.

EXAMPLE 3

The process of Example 1 was repeated using only 0.585 g of decanoyl peroxide. The anhydride copolymer product was then converted to the diacid derivative and its salt, as in Example 2.

EXAMPLE 4

The process of Example 1 was repeated at 75° C. to provide the anhydride copolymer which was then converted to its diacid derivative which was converted to its salt by neutralizing 450.53 g of the polymer solution (diacid 22.08% solids in water) with 40.018 g $CaCO_3$/6.053 g $Na_2CO_3$/120.27 g water, using 217.87 g water for transfer of the salt into the kettle.

Comparative Example

The process of Example 1 was repeated except that the N,N'-1,3-phenylenedimaleimide reactant was omitted. The resultant anhydride copolymer was converted to its diacid and salt derivative as in Example 2.

TEST RESULTS

| EXAMPLE NO. | VISCOSITY* | MW** |
|---|---|---|
| 2 | 6.86 | $1.48 \times 10^6$ |
| 3 | 15.09 | $2.57 \times 10^6$ |
| 4 | 3.60 | $9.5 \times 10^5$ |
| Comparative | 3.21 | $3.7 \times 10^5$ |

*η rel (diacid derivative, $H_2O$, neat)
**as determined by Multi Angle Laser Light Scattering, weight average molecular weight, diacid derivative While the invention has been described with particular reference to certain embodiments thereof, it will be understood that many alterations and modifications may be made which are considered within the scope of this invention and which will become apparent from the foregoing disclosure.

What is claimed is:

1. A high molecular weight homogeneous, branched polymer of maleic anhydride and a $C_1$–$C_5$ alkyl vinyl ether monomers, in which the polymer chains are branched with a branching agent present in an amount of less than 0.5 wt. % of the polymer.

2. A polymer according to claim 1 in which the maleic anhydride is present in the polymer in the form of the half-ester or diacid derivatives.

3. A polymer according to claim 1 in which the molecular weight is greater than 100,000.

4. A polymer according to claim 1 in which the molecular weight is greater than 500,000.

5. A polymer according to claim 1 wherein the molecular weight is greater than 1,000,000.

6. A solution of the polymer of claims 1 or 2.

7. A solution according to claim 6 at greater than 30% solids.

8. A solution according to claim 6 in which the solvent is acetone.

9. A personal care or oral care composition including the polymer of claims 1 or 2.

10. An oral care composition according to claim 9 which is a denture adhesive composition.

* * * * *